United States Patent
Brorson

Patent Number: 5,501,595
Date of Patent: Mar. 26, 1996

[54] MATRIX BAND AND MATRIX RETAINER FOR A FRONT-TOOTH MATRIX

[76] Inventor: Lars Brorson, Drottninggatan 62, SE-252 21 Helsingborg, Sweden

[21] Appl. No.: 236,952

[22] Filed: May 2, 1994

[30] Foreign Application Priority Data

Mar. 3, 1994 [SE] Sweden ..................... 9400744

[51] Int. Cl.$^6$ ..................... A61C 5/12
[52] U.S. Cl. ..................... 433/39
[58] Field of Search ............... 433/39, 40, 41, 433/148, 149, 226

[56] References Cited

U.S. PATENT DOCUMENTS

| | | | |
|---|---|---|---|
| 785,619 | 3/1905 | Leffingwell | 433/39 |
| 2,039,418 | 5/1936 | Hutchinson. | |
| 2,310,448 | 2/1943 | Leib | 433/39 |
| 2,790,238 | 4/1957 | Trangmar. | |
| 3,074,169 | 1/1963 | Freeman | 433/39 |
| 3,421,222 | 1/1969 | Newman | 433/39 X |
| 3,513,545 | 5/1970 | Miller. | |
| 3,812,585 | 5/1974 | Balson | 433/39 |
| 3,829,975 | 8/1974 | Balson | 433/39 |
| 4,563,152 | 1/1986 | McClure | 433/39 |
| 4,824,365 | 4/1989 | von Weissenfluh | 433/39 X |
| 4,909,736 | 3/1990 | Ritter | 433/39 |

FOREIGN PATENT DOCUMENTS

| | | |
|---|---|---|
| 0227590 | 12/1985 | European Pat. Off. . |
| 0291447 | 5/1987 | European Pat. Off. . |
| 8501434 | 10/1983 | WIPO . |
| 9216158 | 3/1991 | WIPO . |
| 9202189 | 2/1992 | WIPO ..................... 433/39 |

*Primary Examiner*—Nicholas D. Lucchesi
*Attorney, Agent, or Firm*—Brumbaugh, Graves, Donohue & Raymond

[57] ABSTRACT

A matrix band for front teeth consists of a plastic band having two parts which extend away from each other as a preferably obtuse angle. In one embodiment, a transition area between the two parts is elastically extensible. In another embodiment, the transition area is plastically extensible. On each side of the transition area there is a substantially inextensible part. A matrix retainer for a matrix band has a tightening element which has a through channel dimensioned for continuous frictional engagement with two substantially inextensible portions of the matrix band which are movable face-to-face through the channel. The matrix retainer also has a locking element for fixation of the two inextensible portions relative to the tightening element.

14 Claims, 2 Drawing Sheets

MATRIX BAND AND MATRIX RETAINER FOR A FRONT-TOOTH MATRIX

BACKGROUND OF THE INVENTION

The present invention generally relates to front-tooth matrices and more particularly to a matrix band and a matrix retainer for disposable front-tooth matrices.

In odontology, dental matrices are used for shaping the outer contour of a filling so as to make it merge naturally into the adjoining surfaces of the prepared tooth.

The demand placed on a matrix band for such a matrix primarily is that it should ensure the making of a filling without any deficiency of material, i.e. where the filling does not reach as far as the natural contour of the tooth, but also prevent exaggerated excess of material, which has to be removed at a later stage. The matrix band should also permit light-curing, i.e. it must be translucent. Generally, it therefore consists of plastic.

One example of a known matrix is described in EP-A1-0 227 590 where a flat matrix band is combined with a retainer in the form of two wedges and a sleeve. The ends of the matrix band are inserted between the two wedges, which in turn are partially inserted in the sleeve. When a loop of the matrix band has been applied around a tooth, the sleeve is moved towards the tooth so as to clamp the wedges to each other and to the band ends within the sleeve, thus clamping the band around the tooth. This results however in unreliable fixation of the band, and this matrix is not suited at all for use on front teeth, since the flat band is unable in this case to satisfy the primary requirement as set out above. This is so, above all, because of the wedge shape of the front teeth with a partly concave palatal side and a convex buccal side.

Another example of a known matrix is described in WO85/01434 where preformed matrix sheeting is used. In view of the considerable variation in shape and size of the teeth in one individual and of the teeth in different individuals, such preformed matrix sheeting is no viable alternative.

Therefore, the commonest method in filling therapy on front teeth is as follows. A flat, flexible matrix band of transparent plastic is used and applied by the dentist in a loop around the tooth concerned. When the filling material has been applied, the dentist holds the band tightly against the tooth with two fingers in order to contour the filling while an assistant is illuminating the filling, for example with visible light, with a view to curing the filling by polymerization. Alternatively, the band is maintained in position for several minutes in order that the filling material should cure chemically. This mode of operation suffers from obvious drawbacks. Thus, it is possible to make only one filling at a time and the risk of excess or deficiency of material is considerable, since it is difficult to properly observe the filling site. This also entails a considerable risk of deficient polymerization in the event light is used for producing it.

SUMMARY OF THE INVENTION

The object of the present invention therefore is to provide a front-tooth matrix and more particularly a matrix band and a matrix retainer for the front-tooth matrix, which satisfy the primary requirements as set out above, i.e. ensure a well-contoured filling. Moreover, the matrix band and the matrix retainer should enable reliable light polymerization and ensure definite fixation of the matrix band relative to the tooth during the curing process. Finally, the matrix band and the matrix retainer should be generally usable on the front teeth of different individuals.

According to the invention, these and other objects are achieved in a matrix band for front teeth, comprising a plastic band having two parts extending away from each other at a preferably obtuse angle, said matrix band being elastically or plastically extensible in a transition area between said two parts and having on each side of the said transition area a substantially inextensible portion.

Such a matrix band is adapted to the special anatomy of front teeth, i.e. their wedge shape with a concave palatal side and a convex buccal side. The inventive matrix band thus is extensible against the concave side and inelastic outside the transition area engaging the concave side. In this manner, the matrix band of the invention can be adapted to the individual anatomy of each tooth. Since the matrix band is substantially inextensible outside the transition area, there will be no deficiency of material in cavities, whether these open approximately or buccally. The inextensible portions also enable reliable fixation of the matrix band around the tooth concerned.

The extensibility in the transition area can be achieved by the matrix band there having reduced thickness or by the matrix band consisting of different materials in and outside the transition area. The most convenient way to achieve the desired adaptability is to combine the extensibility with an obtuse angle between the two parts. It is however possible to use a completely straight band, i.e. whose two parts are aligned with each other, if the extensibility of the transition area is sufficient.

The objects set out above are also achieved by means of a matrix retainer for a matrix band as defined above, comprising a tightening element having a through channel dimensioned for continuous frictional engagement with two substantially inextensible portions of the matrix band which are movable face-to-face through the channel, and a locking element for fixation of said two inextensible portions relative to said tightening element.

Such a matrix retainer provides reliable fixation of the matrix band, especially by being lockable. It is also especially advantageous in that it can be left in any position before locking.

The matrix retainer according to the invention is specially developed and suited for the inventive matrix band. It should however be noted that the inventive matrix retainer can be used together with any elongate matrix band having inextensible portions for frictional engagement with the tightening element of the matrix retainer.

Particularly, the locking element may have engagement means which are movable towards each other for lockingly deforming the two inextensible portions of the matrix band.

In a preferred embodiment, the tightening element and the locking element comprise two substantially identical plastic strips which can be snapped together. To achieve good fixation of the matrix band and the matrix retainer during the curing process, the tightening element may advantageously have a cupped surface surrounding an opening of the channel facing the buccal side of a front tooth.

The inventive dental matrix is of disposable type and, thus, should be discarded after use to prevent infections from spreading. This is ensured by the matrix band being deformed by extension in the transition area and by other, permanent deformation normally being produced when locking the matrix band.

The matrix band according to the invention is usable on front teeth, both in the upper jaw and in the lower jaw, and offers an overall view of the entire insertion and tightening process, both from the buccal and from the palatal side. By the special combination of an extensible transition area and adjacent inextensible portions, the excess and deficiency of filling material will be minimized. Moreover, polymerization of several fillings can be done simultaneously in one or more teeth.

Another advantage of the invention is that the dentist can work without any assistance and even temporarily leave the patient. There is hardly any risk of insufficient polymerization because both the matrix band and the matrix retainer are light-transmitting. The preferred angled shape of the matrix band gives, in combination with the extensible transition area, maximum adaptability to different front-tooth shapes and obviates the risk of gingival wounds.

BRIEF DESCRIPTION OF THE DRAWINGS

An embodiment of a matrix band and a matrix retainer according to the invention will be described in more detail hereinbelow with reference to the accompanying drawings, in which.

DESCRIPTION OF THE PREFERRED EMBODIMENT

Figure 1:
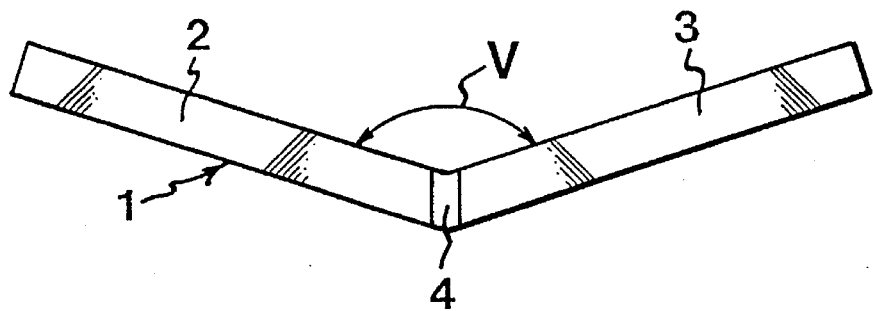
FIG. 1 is a plan view of a matrix band according to the invention.

The matrix band according to the invention shown in plan view in FIG. 1 consists of a flexible plastic band 1 having two parts 2, 3 which extend away from each other at an obtuse angle V. For optimal adaption to an average front-tooth shape, the angle V should be approximately 145°. The matrix band 1 may have a thickness of about 50 µm and a width of about 8 mm.

In the angle-vertex portion between the two parts 2, 3, there is a transition area 4 having a width that is smaller than the width of an average front tooth.

The plastic band 1 consists of light-transmitting plastic to permit light polymerization of a light-curable filling material.

According to the invention, the transition area 4 is elastically or plastically extensible when subjected to such tensile forces as can be manually applied by a dentist when placing the matrix band around a front tooth as will be described further on. The parts 2 and 3 are substantially inextensible, at least in portions on each side of the transition area 4, i.e. as compared with the transition area 4.

The extensibility or deformability of the transition area 4 can be achieved either by making this area thinner than the rest of the matrix band 1, or by making this area from another plastic than the rest of the matrix band 1.

Figure 2:
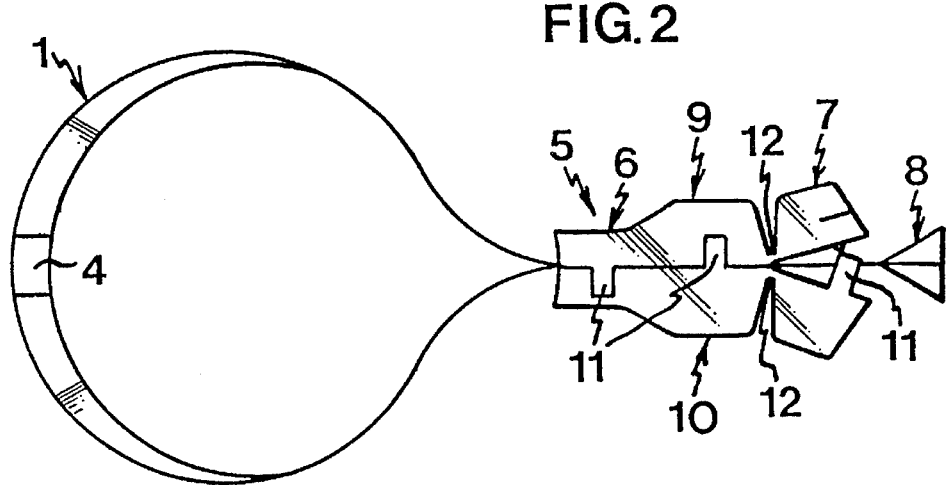
FIG. 2 is a plan view of a matrix retainer according to the invention, combined with the matrix band in FIG. 1.
Figure 3:
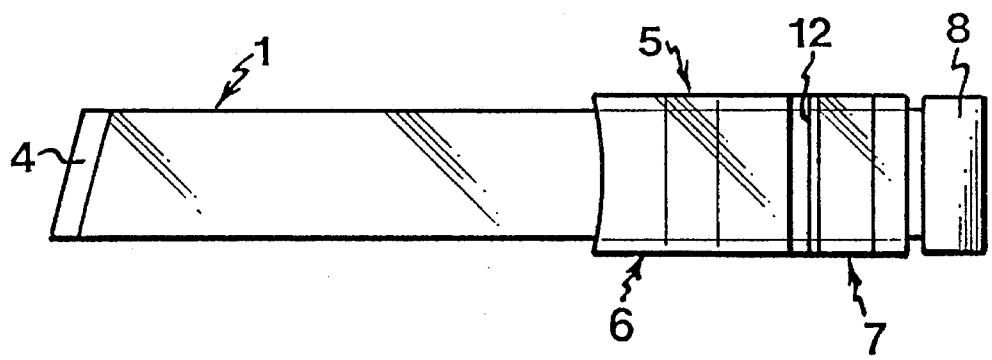
FIG. 3 is a side view of the matrix retainer and the matrix band in FIG. 2.

FIGS. 2 and 3 show the matrix band 1 in FIG. 1 combined with a matrix retainer 5 according to the invention. More specifically, the matrix retainer 5 consists of three parts, namely a tightening element 6, a locking element 7 and a connecting element 8, which is however not compulsory. Each of these elements may consist of two substantially identical halves. Thus, one half of the elements 6–8 may be a strip 9 while the other half of the elements 6–8 may be a substantially identical strip 10. Also the matrix retainer 5 consists of light-transmitting plastic.

Figure 4:
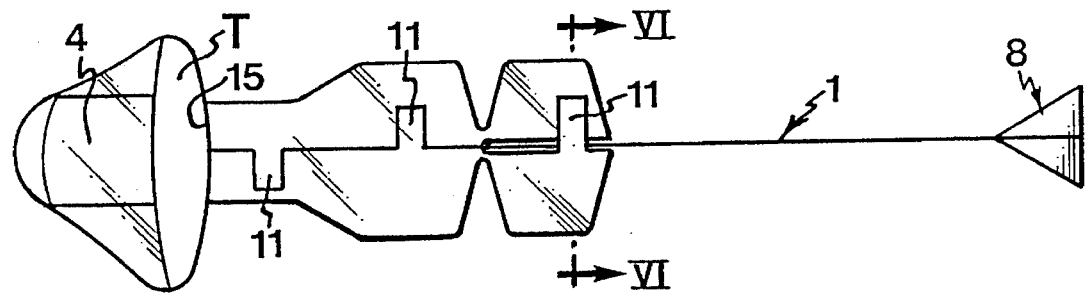
FIG. 4 is a view similar to FIG. 2, but with the matrix band applied around a front tooth.
Figure 6:
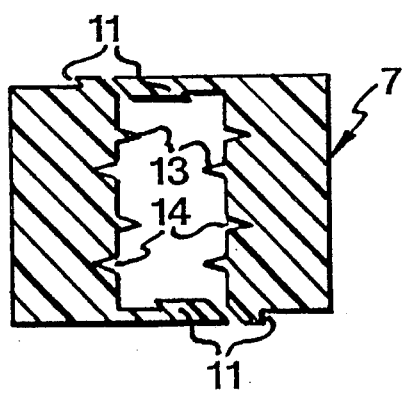
FIG. 6 is a cross-sectional view taken along the line VI—VI in FIG. 4.

By means of the two halves of the connecting element 8, the otherwise free ends of the band 1 can be connected to each other. The strips 9, 10 may be joined together with the aid of a longitudinal hinge joint on one side and with the aid of hook means 11 on the other side. The hook means 11 are shown in FIG. 4. Alternatively, the strips 9 and 10 may be joined together by hook means 11 on both sides, as shown in FIG. 6.

The interconnection of the strips 9, 10 is such that there is defined between them a through channel which, within the tightening element 6, is so dimensioned as to produce a continuous frictional engagement with the two inextensible portions of the band 1, which extend face-to-face through the channel in the tightening element 6.

The locking element 7 in turn is articulated to the tightening element 6 by means of a hinge joint 12 in each strip 9, 10. In the starting position, the two parts of the locking element 7 are slightly parted, as shown in FIG. 2, so that spikes 13 and mating recesses 14 in the opposing surfaces of the two parts of the locking element 7 allow the two parts 2, 3 of the matrix band 1 to move freely.

When using the inventive dental matrix described above, the loop of the matrix band 1 shown in FIG. 2 is first placed over a front tooth to be treated, and is then moved down by a sawing motion on each side of the tooth T and stretched, so that the transition area 4 is located in the middle of the palatal part of the tooth surface, with any palatal parts of the cavities well sealed. The connecting element 8 may then be broken off from the locking element 7. The connecting element 8 is still connected to the ends of the plastic band even after it is broken off the locking element 7. Therefore, when the tightening element 6 is moved away from the connecting element 8, the band will be tightened.

Filling material is thereafter inserted in the cavities, and the matrix retainer 5 is moved towards the buccal surface of the tooth by moving the tightening element 6 away from the connecting element 8. During this movement, the tightening element 6 makes continuous frictional engagement with the portions of the parts 2, 3 of the matrix band 1 which are located in the through channel of the tightening element 6. Thus, the dental matrix can be left at any time during this movement to allow inspection of the cavity filling.

Figure 5:
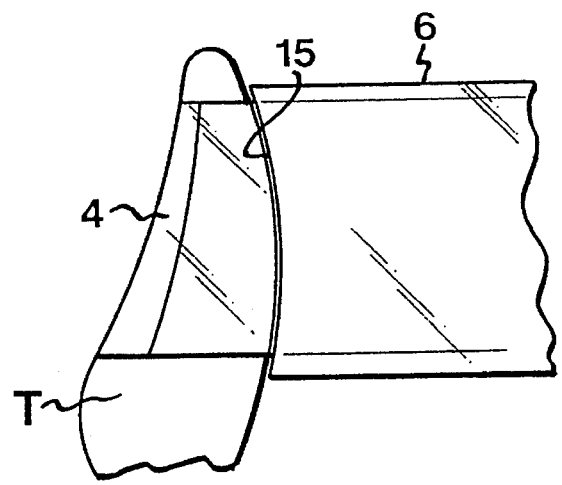
FIG. 5 is a side view of the tooth in FIG. 4 and adjacent parts of the matrix band and the matrix retainer.

When the loop is being finally tightened around the tooth T, as illustrated in FIGS. 4 and 5, such an extension of the transition area 4 is produced that the matrix band 1 is completely adapted to the contour of the tooth T with definite fixation in the horizontal and vertical directions relative to the tooth. This is also ensured by the cupped shape of the front surface 15 of the tightening element 6, which front surface 15 is concave both in the vertical direction and in the horizontal direction to provide good adaption to the buccal surface of a front tooth.

When such optimal adaption has been achieved, the matrix band is locked in place by pressing the two parts of the locking element 7 against each other, so that the spikes 13 while entraining material in the matrix band 1, penetrate into the recesses 14. This results in fixation of the two inextensible portions of the matrix band 1 relative to the tightening element 6. Of course, movable engagement means other than the spikes 13 and the recesses 14 can be used for achieving the locking deformation of the two inextensible portions of the matrix band. The inextensible portions of the matrix band 1 must thus extend at least from the transition area 4 up to and through the locking element 7.

Once the matrix band is fixed and locked around the tooth, the dentist is free to polymerize the filling with light or to do other work in the case of chemical curing alone. The dentist can thus apply several matrices on different teeth to restore several teeth at a time.

When curing or polymerization is completed, the locking element 7 can be opened with a nail or a flat instrument, whereupon the tightening element 6 can be pulled away from the tooth and the matrix band 1 be lifted off the tooth to make this available for conclusive treatment of the filling. The entire dental matrix is discarded for recycling.

The matrix band and the matrix retainer described above can of course be modified in many respects within the scope of the invention, such as it is defined in the appended claims.

What I claim and desire to secure by Letters Patent is:

1. A front tooth matrix band for fillings in proximally and buccally opening cavities, comprising:

a bendable plastic single-layer band having a central transition area for overlying the middle of the palatal side of a front tooth, the transition area being extensible and extending entirely across the band in a width-wise direction, and two substantially inextensible parts joined by the transition area for overlying the proximal and the buccal sides of the front tooth, the inextensible parts forming, when the band lies flat in a plane, an obtuse angle in the plane, the matrix band being substantially completely conformable to the contour of a front tooth by tightening the matrix band as a loop around the tooth with said transition area engaging the middle of the palatal side of the front tooth while portions of said inextensible parts on each side of said transition area engage the proximal and buccal sides of the tooth.

2. A matrix band as claimed in claim 1, wherein the width of the transition area is smaller than the width of an average front tooth.

3. A matrix band as claimed in claim 1, wherein the transition area has reduced thickness.

4. A matrix band as claimed in claim 1, wherein the transition area comprises a material different from the material of said two parts.

5. A matrix band as claimed in claim 1, wherein the obtuse angle is about 145°.

6. The front tooth matrix band of claim 1, wherein said transition area is plastically extensible.

7. The front tooth matrix band of claim 1, wherein said transition area is elastically extensible.

8. A matrix retainer for a bendable plastic matrix band that has a central and extensible transition area and two substantially inextensible parts joined by said transition area, comprising:

a tightening element having a through channel having a width corresponding substantially to and adapted to receive the two substantially inextensible parts in face-to-face contact with each other such that the two substantially inextensible parts are movable through the channel in face-to-face contact with each other and are in frictional engagement with the channel, and engagement means having locking members movable towards each other for locking the two inextensible parts relative to the tightening element by deformation of portions of the two inextensible parts while they are maintained by the members in face-to-face contact with each other, wherein said tightening element and said locking element comprise two substantially identical, interconnectible plastic strips.

9. A matrix retainer as claimed in claim 8, wherein the tightening element has a vertically cupped surface surrounding an opening of said channel.

10. A front tooth matrix for fillings in proximally and buccally opening cavities, comprising:

a bendable plastic single-layer band having a central and extensible transition area for overlying the middle of the palatal side of a front tooth, the transition area extending entirely across the band in a width-wise direction, and two substantially inextensible parts joined by said transition area for overlying the proximal and the buccal sides of the front tooth, the parts forming, when the band lies flat in a plane, an obtuse angle in the plane;

a tightening element having a through channel receiving said two substantially inextensible parts in face-to-face contact with each other such that the plastic band forms a loop outside one end of the channel, said through channel having a width corresponding substantially to the thickness of the two substantially inextensible parts in face-to-face contact with each other, the two substantially inextensible parts being movable through the channel in face-to-face contact with each other and in frictional engagement with the channel; and engagement means having members movable towards each other for locking the two inextensible parts relative to the tightening element by deformation of portions of the two inextensible parts while they are maintained by the members in face-to-face contact with each other, the matrix band being substantially completely conformable to the contour of a front tooth by placing said loop around the tooth and tightening the matrix band by means of said tightening element with said transition area overlying and engaging the middle of the palatal side of the front tooth while portions of the inextensible parts on each side of said transition area engage the proximal and buccal sides of the tooth, and said engagement means locking said two inextensible parts relative to the tightening element to maintain the matrix band pressed against the tooth.

11. The front tooth matrix of claim 10, wherein said engagement means comprises cooperating spikes and recesses.

12. The front tooth matrix of claim 10, further comprising an element connecting ends of the inextensible parts remote from the transition area to each other.

13. A matrix band for front teeth comprising:

a central transition area, the transition area being substantially extensible and smaller than the width of an average front tooth;

two parts connected to opposite sides of the transition area and extending away from each other at a substantially obtuse angle, the two parts being substantially inextensible;

the transition area being constructed of a material different from the material of the two parts.

14. The combination comprising:

a bendable plastic matrix band having a central and extensible transition area and two substantially inextensible parts joined by said transition area, the substantially inextensible parts forming, when the band lies flat in a plane, an obtuse angle in the plane;

a tightening element having a through channel receiving said two substantially inextensible parts in face-to-face contact with each other such that the plastic band forms a loop outside one end of the channel, said through channel having a width corresponding substantially to the thickness of the two substantially inextensible parts in face-to-face contact with each other, the two substantially inextensible parts being movable through the channel in face-to-face contact with each other and in frictional engagement with the channel; and engagement means having members movable towards each other for locking the two inextensible parts relative to the tightening element by deformation of portions of the two inextensible parts while they are maintained by the members in face-to-face contact with each other, the engagement means being cooperating spikes and recesses, the matrix band being substantially completely conformable to the contour of a front tooth by placing said loop around the tooth and tightening the matrix band by means of said tightening element with said transition area overlying and engaging the middle of the palatal side of the front tooth while portions of the inextensible parts on each side of said transition area engage the proximal and buccal sides of the tooth, and said engagement means locking said two inextensible parts relative to the tightening element to maintain the matrix band pressed against the tooth.

* * * * *